United States Patent [19]

Mayrhofer et al.

[11] Patent Number: 5,639,662
[45] Date of Patent: Jun. 17, 1997

[54] INCREASED ENANTIOSELECTIVITY OF LIPASE CATALYZED TRANSESTERIFICATION OF ALKYNOLS WITH VINYL ESTERS

[75] Inventors: Herbert Mayrhofer, Engerwitzdorf; Irma Wirth, Enns; Peter Pöchlauer, Linz, all of Austria

[73] Assignee: DSM Chemie Linz GmbH, Linz, Austria

[21] Appl. No.: 529,712

[22] Filed: Sep. 18, 1995

Related U.S. Application Data

[63] Continuation of Ser. No. 198,772, Feb. 18, 1994, abandoned.

[30] Foreign Application Priority Data

Feb. 19, 1993 [AT] Austria .................................. 319/93

[51] Int. Cl.$^6$ ............................................. C12P 41/00
[52] U.S. Cl. ........................... 435/280; 435/135; 435/155
[58] Field of Search ........................ 435/280, 135, 435/155

[56] References Cited

U.S. PATENT DOCUMENTS 4,963,492  10/1990  Keller et al. ............................ 435/280

FOREIGN PATENT DOCUMENTS

| 0 290 878 | 11/1988 | European Pat. Off. . |
| 37 24 899 | 12/1988 | Germany . |
| 41 00 394 | 7/1992 | Germany . |
| 41 31 546 | 3/1993 | Germany . |
| 5-84094 | 4/1993 | Japan . |

OTHER PUBLICATIONS

Zaks A et al, Proc. Natl Acad Sci 82:3192–96 (1985).
Okumura S et al, BBA 575: 156–165 (1979).
Hills M J et al, BBA 1042: 237–240 (1990).
Jeromin G E et al, Tetrahedron Lett 32: 7021–24 (1991).
Baxter Catologue p. C187 (1989).
SIGMA Catalog pp. 610, 611 (1992).
Fujiwara A et al, Chem Express 7: 765–8 (1992).
"J. Am. Chem. Soc." 112, 7434–7436 (1990).
Patent Abstracts of Japan, C–911, Feb. 18, 1992, 16, No. 63: JP 3–259004.

Primary Examiner—Sandra E. Saucier
Attorney, Agent, or Firm—Wenderoth, Lind & Ponack

[57] ABSTRACT

Process for enhancement of enantioselectivity in the enzymatic separation of (R)- and (S)-enantiomers of an asymmetric alkynol, a lipase and in the presence of at least one vinyl ester, in which the acid component has at least 4 C atoms, an organic solvent and with the addition of water. Also disclosed is a process for enhancement of enantioselectivity in the enzymatic separation of (R)- and (S)-enantiomers of an alcohol with the aid of the abovementioned vinyl ester under addition of a second vinyl ester having at least 2 C atoms less in the alkyl chain than the vinyl ester used as esterifying agent.

10 Claims, No Drawings

INCREASED ENANTIOSELECTIVITY OF LIPASE CATALYZED TRANSESTERIFICATION OF ALKYNOLS WITH VINYL ESTERS

This application is a continuation of now abandoned application Ser. No. 08/198,772, filed Feb. 18, 1994.

Optically active alkynols are important intermediates in the synthesis of e.g. pheromones or pharmaceutically active compounds. The biological or pharmaceutical activity of such compounds thereby depends on the configuration of the carbon atom which carries the hydroxyl group because usually only one of the possible configurations exerts the desired activity. Therefore the synthesis of the enantiomerically pure alkynols is of great importance.

Methods for the enzymatic racemate resolution of asymmetric alkynols are known. According to Chemistry and Physics of Lipids, 54 (1990), 43 to 48 an asymmetric alkynol is esterified using a carboxylic acid and the racemic mixture of esters thus obtained is hydrolysed enantioselectively in the presence of a lipase. Thereby the entire mixture has to be esterified chemically prior to the enzymatic separation of the enantiomers.

In EP-A-0 290 878 the conversion of a mixture of (R)- and (S)-1-trimethylsilyl-1-butyn-3-ol into the corresponding (S)-alcohol and into the corresponding (R)-ester by enantioselective esterification using a glycerol triester in the presence of a hydrolase to achieve a separation of the enantiomers is disclosed. During this reaction however alcohol groups of the glycerol triester are deacylated. Since each hydrolase effects esterification until an equilibrium is reached, the deacylated alcohol groups can be re-esterified leaving the desired esterification of the alkynol incomplete. In J. Am. Chem. Soc. 1990, 112, 7434 to 7436 there is suggested to use vinyl acetate for the racemate resolution of (R,S)-alkynols to avoid this re-esterification. The vinyl alcohol which is generated by this reaction tautomerizes to give acetaldehyde which does not affect the reaction rate. This method however is restricted to alcohols which carry at the asymmetric carbon atom one relatively large and one relatively small substituent because only in such cases acceptable selectivities are obtained.

In U.S. Pat. No. 4,963,492 a method for the enzymatic racemate resolution of alcohols in the presence of a lipase and in the presence of vinyl acetate or vinyl chloroacetate as esterifying agent is described. In one example the racemate resolution of (R,S)-1-octyn-3-ol is disclosed. The selectivities achieved are, however, dissatisfying.

It has now been found that far higher selectivities can be obtained by using a vinyl ester in which the acid component consists of at least four carbon atoms instead of using vinyl acetate. Thereby it is no longer necessary to have a large and a small substituent bonded to the asymmetric carbon atom.

Therefore, the invention provides a process for enhancing enantioselectivity in a process for the separation of the (R)- and (S)-enantiomers of an asymmetric alkynol of the formula

  I in which R and $R_1$ independently of each other denote alkyl groups having 1 to 10 C atoms and in which R additionally denotes hydrogen, in the presence of a lipase and in the presence of a vinyl ester as esterifiying agent, comprising employing as esterifying agent at least one vinyl ester of the formula $CH_2=CH-O-CO-R_2$  II in which $R_2$ denotes an alkyl group having at least 3 C atoms.

By asymmetric alkynol an alkynol having one C atom substituted by one hydrogen atom, one alkyl group, one alk-1-ynyl group and one hydroxyl group is to be understood.

In the formula I R and $R_1$ denote alkyl groups having 1 to 10, preferably 1 to 8 C atoms, and R additionally denotes hydrogen. Preferred are straight chain alkyl groups, for example methyl, ethyl, n-butyl, n-octyl groups. Especially preferred are compounds in which R denotes hydrogen and $R_1$ denotes an alkyl group having 1 to 4 C atoms. Such alkynols are known and/or can be prepared by known methods. The asymmetric alkynol can be used as racemic mixture or as a mixture in which one of the enantiomers is enriched.

In the formula II $R_2$ denotes an alkyl group preferably a straight chain alkyl group having at least 3, preferably 3 to 15, especially 3 to 11 C atoms. Especially preferred are vinyl butyrate, vinyl octanoate, vinyl laurate. Vinyl esters are commercially available or can be prepared by known methods.

As lipase a lipase suitable for racemate resolutions is to be understood. Preferred is a lipase from pig liver, porcine pancreas and from microorganisms such as Candida, Mucor, Rhizopus, Penicillium, Aspergillus, Pseudomonas. Especially preferred is a commercially available lipase, especially from Candida or from Pseudomonas. The lipase may be used in purified or partially purified form or in form of the microorganism itself, it may be used as such or in immobilized form and is preferably used as such or immobilized.

The process can be performed as disclosed in EP-A-0 321 918: A lipase and an alkynol of the formula I are reacted with a vinyl ester of the formula II. At least one half equivalent of vinyl ester is added per equivalent of alkynol. Generally the vinyl ester is not only used as reactant, but also as diluent and is therefore used in higher quantities. Long chain vinyl esters of formula II are often viscous. High viscosity of the reaction mixture has, however, a negative impact on the reaction rate. Therefore the excess of the vinyl ester related to the alkynol is to be kept so small that an increase of viscosity to an extent which would lower the reaction rate is avoided. The required amount of the lipase depends on the chemical nature of the alkynol and of the vinyl ester, on the desired reaction time and on the nature of the lipase. It can easily be determined by pilot tests.

The reaction mixture is stirred or shaken together with the lipase at a temperature between −10° C. and the deactivation temperature of the lipase used, preferably at a temperature at which the lipase shows its highest activity. This temperature is usually disclosed by the producer. It is, however, also possible to place the lipase in a module, for example in a column, and to circulate the mixture containing the alkynol and the vinyl ester through this module. In doing so, one of the two alkynol enantiomers is preferentially converted into the ester, whereas the second enantiomer remains unconverted as alcohol. Thereby the vinyl ester is converted into the corresponding vinyl alcohol which tautomerizes into the corresponding aldehyde.

The progress of the reaction is monitored by usual methods, for example by gas chromatography. A lipase converts preferentially one of the two enantiomers, but the second enantiomer is generally also converted. Therefore the enantiomeric excess ee of the unreacted alcohol or of the produced ester is determined in suitable intervals by suitable methods for example by determination of the optical rotation or by chromatography on a chiral phase. After the desired degree of conversion, which depends on the desired enantiomeric excess, is obtained, the reaction is stopped. If necessary, the lipase is separated from the reaction mixture by filtration or centrifugation. The residue is submitted to a separation procedure such as extraction, distillation or chromatography. Preferred is a distillation, which is generally especially effective, because it was found that the boiling points of the alcohol, of the ester, of the vinyl ester and of the aldehyde emerging from the vinyl ester differ sufficiently for a highly effective separation. If the desired alkynol enantiomer is esterified in the course of the reaction, the esterified enantiomer can be separated from the reaction mixture and cleaved by known methods to give the desired alkynol enantiomer in pure or at least in enriched form.

Unexpectedly it has been found that the addition of an organic solvent to the reaction mixture positively influences the reaction rate as well as the selectivity of the reaction. Therefore, in a preferred embodiment of the invention, an organic solvent is added to the reaction mixture. In this case only 0.5 to 1.5 equivalents, preferably 1.0 to 1.3 equivalents of vinyl ester of formula II are used per equivalent of alkynol of the formula I. One advantage of the process of the invention is that the vinyl ester of the formula II has not to be used as solvent but merely as reactant. A part of the vinyl ester can thereby be replaced by an organic solvent which is more readily available. Furthermore by addition of an organic solvent a viscous reaction mixture, which is undesired, is avoided. Suitable organic solvents are for example aliphatic or aromatic hydrocarbons which can be substituted by halogen, such as pentane, hexane, cyclopentane, toluene, xylenes, dichloromethane, dichloroethane, chlorobenzenes, ethers such as diethyl ether, tetrahydrofuran, dioxane, esters such as butyl acetate or ethyl acetate or mixtures of said solvents. Halogenated hydrocarbons or aromatic hydrocarbons are preferred. The organic solvent is added in amounts of 0.1 to 70 vol % preferably of 0.5 to 60 vol % of the entire volume of the reaction mixture.

Furthermore it was completely unexpectedly found, that in a process for the separation of the (R)- and (S)- enantiomers of an asymmetric alkynol with the aid of a vinyl ester of the formula II, enantioselectivity also may be enhanced, if a second vinyl ester of the formula II in which $R_2$ denotes at least 2 C-atoms in the alkyl chain less than $R_2$ in the vinyl ester used as reagent, is added into the reaction mixture in catalytic amounts. Thus it was found that the enantioselectivity of the reaction of an alkynol of the formula I with vinyl laurate was significantly enhanced after addition of 1 percent by weight of vinyl butyrate based on vinyl laurate. It was additionally found that this surprising catalytic effect of enhancement of enantioselectivity due to the addition of the second vinyl ester not only arises in the racemate resolution of alkynols of the formula I, but arises generally in a process for the enzymatic separation of alcohol racemates with the aid of a vinyl ester. The addition of the second vinyl ester however is preferred in the separation of alkynols of the formula I.

A further object of the invention is therefore a process for enhancing enantioselectivity in an enzymatic process for the separation of (R)- and (S)-enantiomers of an alcohol in the presence of a lipase and in the presence of a vinyl ester of the formula

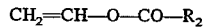    II in which $R_2$ denotes an alkyl group having at least 3 C atoms as esterifying agent comprising adding a catalytical amount of a second vinylester of the formula II in which the alkyl chain has at least 2 C-atoms less than the vinylester of the formula II used as esterifying agent.

The difference in the length of the alkyl chain of the vinyl ester of the formula II and of the vinyl ester added in catalytic amount only is at least 2 C-atoms for achieving an enhancement in enantioselectivity. Preferred is a difference in the length of the alkyl chain of at least 4, particularly preferred of 6 to 10 C-atoms. A catalytical addition of vinyl butyrate to vinyl esters of the formula II, in which $R_2$ denotes at least 8, preferred at least 10 alkyl groups was shown to be particularly favorable. Catalytic amounts are intended to mean amounts which are not at all sufficient for the separation of the racemic mixture. Preferred is the addition of the second vinyl ester in an amount of 0.1 to 5.0, particularly preferred of 0.5 to 4.0 percent by weight based on the vinyl ester of the formula II used as esterifying agent.

Moreover it was surprisingly found that the addition of water to the reaction mixture in an amount of 0.03 to 0.5 vol %, preferably 0.1 to 0.3 vol % of the entire reaction mixture enhances the reaction rate. Therefore in a preferred embodiment of the invention 0.05 to 0.5 vol % of water are added to the reaction mixture. In an especially preferred embodiment of the invention one mol of 3-butyn-2-ol is mixed with 1.0 to 1.5 mol of vinyl butyrate or of vinyl laurate with a content of 0.1 to 5.0 percent by weight of vinyl butyrate, 60 vol % of dichloromethane and 0.3 vol % of water, all based on the entire reaction mixture, and the reaction mixture is circulated at a temperature of 15° to 50 ° C. through a module charged with a lipase from Candida or Pseudomonas. The reaction is stopped at the desired degree of conversion which is determined as pointed out above and the reaction mixture is submitted to fractional distillation.

By the process according to the invention a mixture of (R)- and (S)- alkynol is converted into a mixture which contains one enantiomer as alcohol and the second enantiomer as ester with high selectivity, whereupon the enantiomers can be separated by a simple, physical separation process. The process of the invention represents therefore an enrichment in the art.

EXAMPLE 1

A mixture of 50 g (R,S)-3-butyn-2-ol (0.713 mol), 209.8 g vinyl laurate (0.927 mol), 460 ml dichloromethane and 0.3 vol % of water based on the entire reaction mixture was circulated through a module charged with 10 g of lipase "Amano PS" from Pseudomonas. The progress of the reaction and the enantiomeric excess ee of the (S)-3-butyn-2-ol was determined by gas chromatography. After 119 hours a conversion of 80% and an ee of the unconverted (S)-3-butyn-2-ol of 91% was obtained.

The reaction mixture was distilled in vacuo and nitrogen was bubbled through the residue of the distillation to gain further (S)-3-butyn-2-ol. All distillates which contained (S)-3-butyn-2-ol were collected and redistilled using a vigreux column under normal pressure. The main fraction was collected at a temperature of 104° to 108° C. 4.8 g of (S)-3-butyn-2-ol (48% of the unconverted (S)-3-butyn-2-ol) with an ee of 91% were recovered.

EXAMPLE 2

3.8 g of (R,S)-3-butyn-2-ol (54.2 mmol), 45 ml dichloromethane, 0.3 ml water and 0.8 g lipase Amano PS from Pseudomonas were stirred for half an hour. 12 g of vinyl octanoate (70.5 mmol) were added and the mixture was shaken at 40° C. for 70 hours, whereafter a conversion of 80% was obtained. The enantiomeric excess of the unconverted (S)-3-butyn-2-ol amounted to 96%. The enzyme was filtered off through celite and the filtrate was distilled. 0.36 g of (S)-3-butyn-2-ol (47% of the unconverted (R,S)-3-butyn-2-ol) with an enantiomeric excess of 96% were obtained.

EXAMPLE 3

7.13 mmol of a racemic alkynol were mixed with 0.02 ml of water, 9.3 mmol of vinyl ester, 6.0 ml of dichloromethane and 0.1 g of lipase "Amano PS" from Pseudomonas and shaken at 37° C. The progress of the reaction was monitored by gas chromatography using a cyclodextrin column. After about 20 hours the reaction was stopped. The results shown in table 1 were thereby obtained:

TABLE 1

| alkynol | vinyl ester | ee alcohol | ee ester |
| --- | --- | --- | --- |
| 1-pentyn-3-ol | vinyl acetate | 29% | 43% |
| 1-pentyn-3-ol | vinyl butyrate | 50% | 28% |
| 1 pentyn-3-ol | vinyl laurate | 61% | 86% |

In Table 1 denotes:
ee alcohol: enantiomeric excess of the unconverted (S)-alkynol
ee ester: enantiomeric excess of the (R)-alkynyl ester produced by the enzyme

EXAMPLE 4

0.5 g (R,S)-1-octyn-3-ol (4.0 mmol) were mixed with 0.025 ml of water, 0.59 g of vinyl butyrate (5.15 mmol), 4.5 ml of dichloromethane and 0.1 g of lipase "Amano PS" and shaken at 37° C. After 17 hours (S)-1-octyn-3-ol with an enantiomeric excess ee of 55% and (R)-oct-1-yn-3-yl butyrate with an enantiomeric excess ee of 71% were obtained.

EXAMPLE 5

5 g of (R,S)-3-butyn-2-ol were mixed with 10.6 g vinyl butyrate, 60 ml of dichloromethane and 1.0 g of lipase Amano P from Pseudomonas and shaken at 40° C. After 195 hours a conversion of 47% was obtained. The unconverted (S)-3-butyn-2-ol had an enantiomeric excess of 49%. In the described manner but with the addition of 0.4 ml of water (0.5% of the entire volume of the reaction mixture) a conversion of 78% was obtained after 92.5 hours. The enantiomeric excess of the unconverted (S)-3-butyn-2-ol amounted to 93%.

EXAMPLE 6

As described in example 3, but using equivalent amounts of vinyl laurate instead of vinyl butyrate (S)-3-butyn-2-ol with an enantiomeric excess of 70% was obtained after 74 hours.

In the described manner but using vinyl laurate containing 1.7 mol % vinyl butyrate (based on vinyl laurate) instead of vinyl laurate an enantiomeric excess of >98% of the unconverted (S)-3-butyn-2-ol was obtained after 85.5 hours.

EXAMPLE 7

A mixture of 10 g of (R,S)-3-butyn-2-ol, 42 g of vinyl laurate (0.186 mol), 90 ml of o-xylole, 0.4 ml of vinyl butyrate and 0.4 ml of water was circulated through a module charged with 6 g of lipase "Amano PS" from Pseudomonas and 6 g of celite at 40 C. After 5.5 hours (S)-3-butyn-2-ol having an enantiomeric excess of 95% was isolated from the reaction mixture.

EXAMPLE 8

Was carried out as described in example 7, but adding an enzym immobilisate, obtained by adsorptive binding of 6 g of lipase "Amano PS" from Pseudomonas onto the synthetic material EP 100, into the reaction mixture and shaking instead of circulating the reaction mixture through a module. After 21 hours at 40° C. (S)-3-butyn-2-ol having an enantiomeric excess of 90% was isolated from the reaction mixture.

EXAMPLE 9

1 g of (R,S)-3-butyn-2-ol, 4.2 g of vinyl laurate, 9 ml of o-xylol, 0.04 ml of vinyl butyrate and 0.01 ml of water were mixed and shaked with 6 g of Novo-enzyme SP 524 and 6 g of celite at 40° C. After 28 hours the enantiomeric excess ee of the non-reacted (S)-3-butyn-2-ol amounted to 63%.

Conversion and enantiomeric excess were determined by gas chromatography, the enantiomeric excess by use of a chiral cyclodextrin column.

What we claim is:

1. A process for enhancing enantioselectivity in an enzymatic process comprising adding 0.05 to 0.5% by volume of water based on the entire reaction mixture to a reaction mixture comprising a racemic alkynol of the formula $$R-C\equiv C-CH(OH)-R_1 \qquad I$$

in which R and $R_1$ independently of each other are alkyl groups having 1 to 10 C atoms and in which R additionally is hydrogen, at least one vinyl ester of the formula $$CH_2=CH-O-COR_2 \qquad II$$

in which $R_2$ is an alkyl group having at least 3 C atoms, an organic solvent, and a lipase capable of catalyzing the reaction, allowing the lipase to catalyze the reaction, and recovering at least one of the enantiomers.

2. The process as claimed in claim 1, wherein the vinyl ester is a mixture of vinyl esters of formula II of different chain length, consisting of 95 to 99.9 weight % of a first vinyl ester of formula II, in which $R_2$ is an alkyl group having at least 5 carbon atoms and of 0.1 to 5% by weight of the total amount of the mixture of vinyl esters of a second vinyl ester of formula II, wherein $R_2$ is an alkyl group at least 2 carbon atoms less in the alkyl chain than the first vinyl ester.

3. The process as claimed in claim 2, wherein the mixture of vinyl esters is a mixture of vinyl laurate and of vinyl butyrate.

4. The process as claimed in claim 1, wherein the organic solvent is in an amount of 0.1 to 60 vol. % based on the entire reaction mixture.

5. The process as claimed in claim 1, wherein the organic solvent is an aliphatic, halogenated hydrocarbon or an aromatic hydrocarbon.

6. The process as claimed in claim 1, wherein R and $R_1$ are independently of each other an alkyl group having 1 to 8 C atoms and in which R additionally is hydrogen.

7. The process as claimed in claim 1, wherein R is hydrogen.

8. The process as claimed in claim 1, wherein $R_2$ is a straight chain alkyl group having 3 to 15 C atoms.

9. The process as claimed in claim 1, wherein the lipase is from a microorganism of the genus Pseudomonas or Candida.

10. The process as claimed in claim 1, wherein at least one of the enantiomers is recovered by distillation.

* * * * *